United States Patent [19]
Kane et al.

[11] Patent Number: 5,342,330
[45] Date of Patent: Aug. 30, 1994

[54] ASSEMBLIES FOR COLLECTING URINE AND OTHER BODY FLUIDS

[76] Inventors: Patricia B. Kane, 4529 Hitching Post Trial, Rockford, Ill. 61101; June G. Halvorson, 4068 Caraway Ct., Loves Park, Ill. 61111

[21] Appl. No.: 983,244

[22] Filed: Dec. 1, 1992

Related U.S. Application Data

[63] Continuation of Ser. No. 694,364, May 1, 1991, abandoned.

[51] Int. Cl.⁵ .................................................. A61F 5/44
[52] U.S. Cl. .................................. 604/329; 128/761; 4/144.1
[58] Field of Search ............... 604/349–353; 220/329–331, 212.5, 337, 339, 752, 756, 764, 212.5, 773; 4/144.1–144.3; 128/760, 761; 206/549, 569, 268; D3/78; D19/76, 77

[56] References Cited

U.S. PATENT DOCUMENTS

| | | |
|---|---|---|
| Re. 28,278 | 12/1974 | Borse ........................ 4/144.2 |
| D. 217,793 | 6/1970 | Hachmeister . |
| D. 258,311 | 2/1981 | Peterson . |
| D. 306,648 | 3/1990 | Jones et al. . |
| 2,628,054 | 2/1953 | Fazakerley . |
| 3,335,714 | 8/1967 | Giesy . |
| 3,473,172 | 10/1969 | Friedman et al. . |
| 3,518,164 | 6/1970 | Andelin et al. .................. 128/760 |
| 3,575,225 | 4/1971 | Muheim . |
| 3,625,654 | 12/1971 | Van Duyne . |
| 3,737,244 | 4/1973 | Collins . |
| 3,909,092 | 9/1975 | Kiernan ........................ 220/339 |
| 3,927,426 | 12/1975 | Geddes . |
| 4,129,131 | 12/1978 | Nattulin ........................ 128/767 |
| 4,241,017 | 12/1980 | Balistreri et al. .................. 128/760 |
| 4,492,258 | 1/1985 | Lichtenstein et al. ............ 604/329 |
| 4,531,245 | 7/1985 | Lowd et al. .................... 4/144.3 |
| 4,687,129 | 8/1987 | Cugley . |
| 4,696,067 | 9/1987 | Woodward ...................... 128/761 |
| 4,805,635 | 2/1989 | Korf et al. ...................... 128/767 |
| 4,989,742 | 2/1991 | Powell . |
| 5,078,296 | 1/1992 | Amidzich ........................ 220/339 |

FOREIGN PATENT DOCUMENTS 0080282   2/1933   Sweden ........................ 4/144.1

OTHER PUBLICATIONS

Card Index Boxes Ad. received Aug. 1969.
*Harriet Carter* gift catalog (1990); p. 117.

Primary Examiner—Randall L. Green
Assistant Examiner—Rob Clarke
Attorney, Agent, or Firm—Ryan, Kees & Hohenfeldt

[57] ABSTRACT

An assembly for handling a collection container for urine or another body fluid includes a container having a chamber with an opening for receiving fluid and a hinged lid for opening and closing the container. The hinge includes a bracing mechanism that abuts against and buttresses the lid against movement beyond a preselected position in which the lid forms a outwardly extending handle that supports the container in a fixed upright attitude for receiving fluids. The same structure therefore can serve both as a lid and as an handle for the collection container.

10 Claims, 2 Drawing Sheets

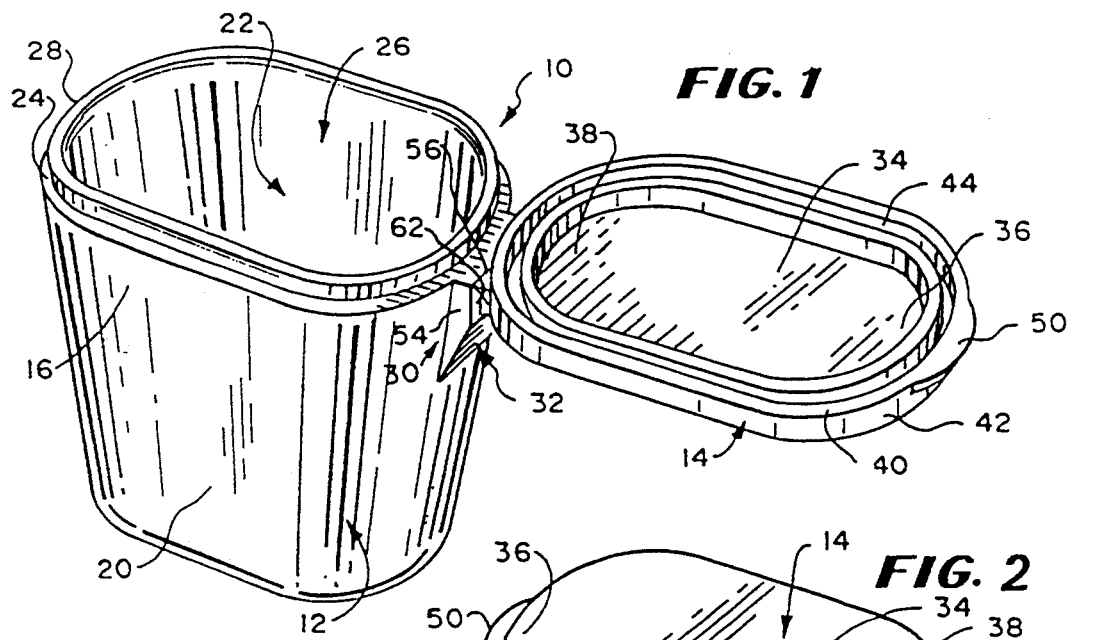
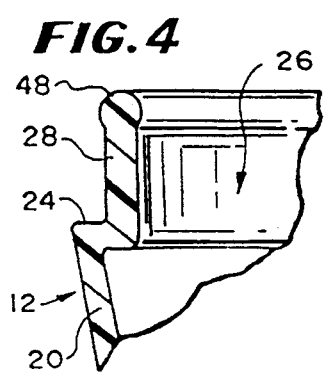
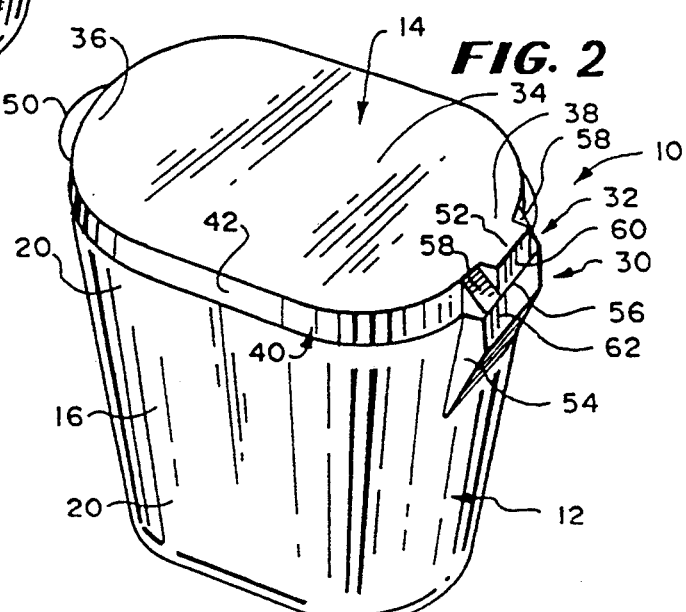
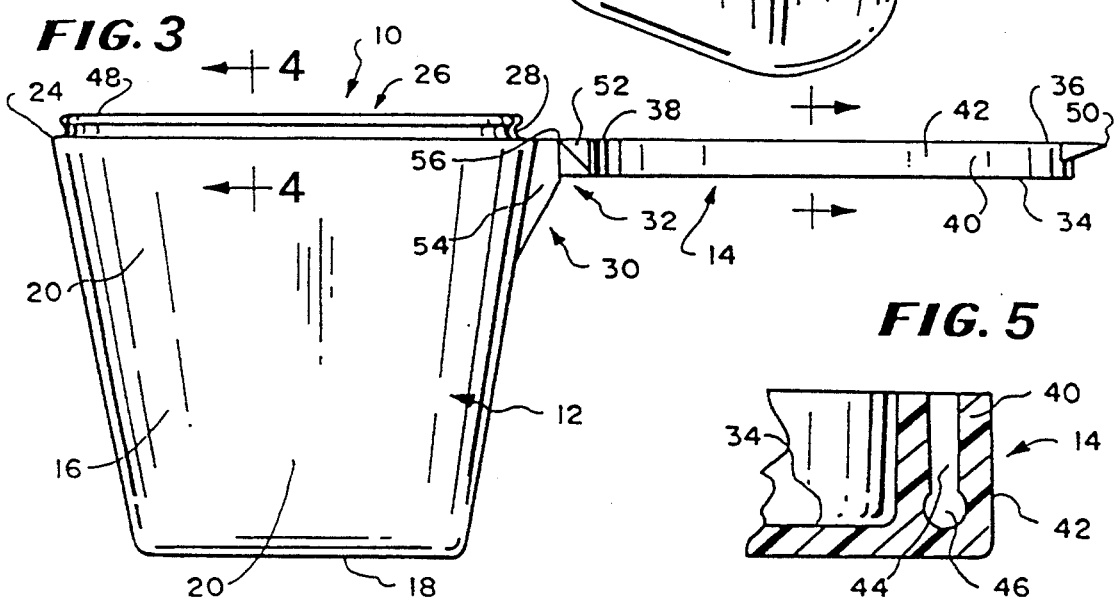

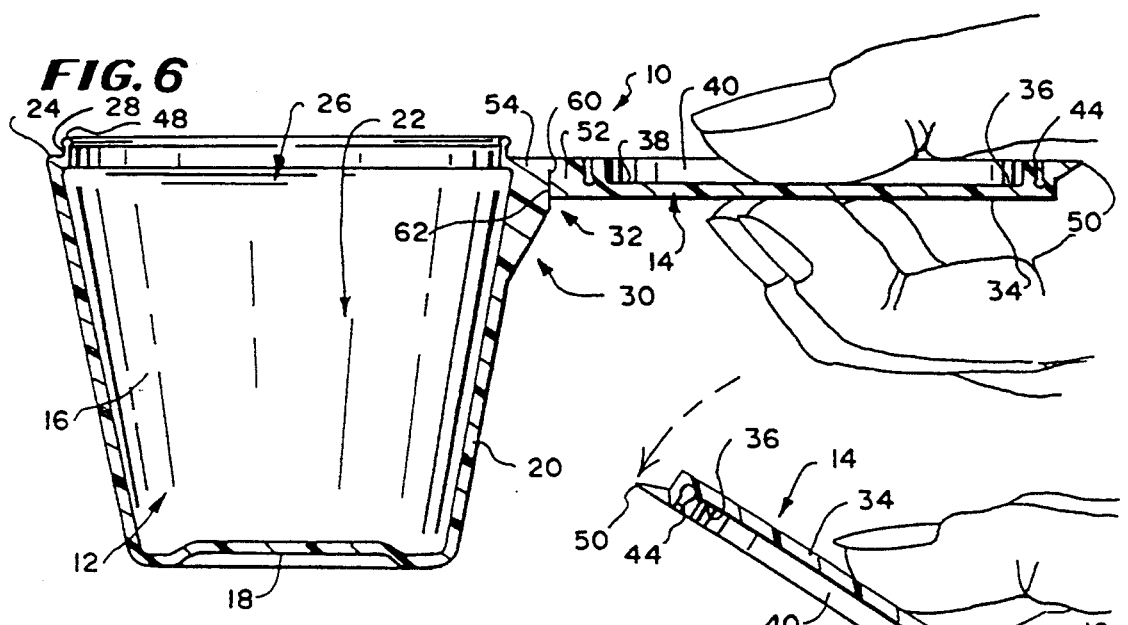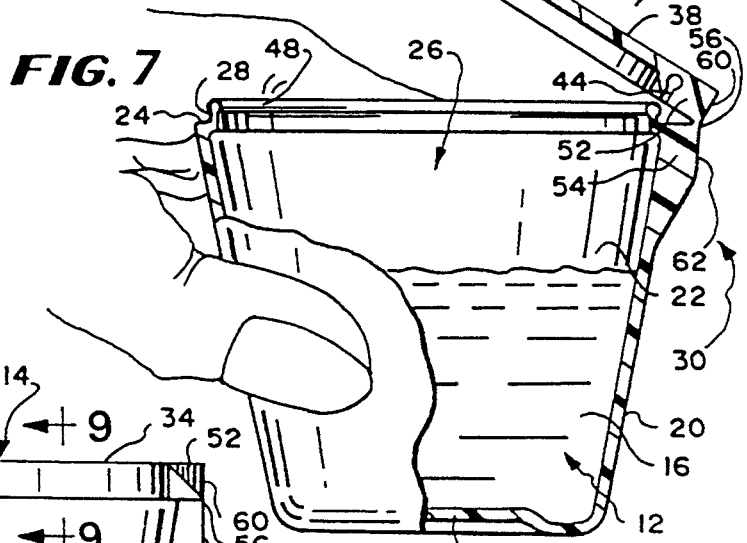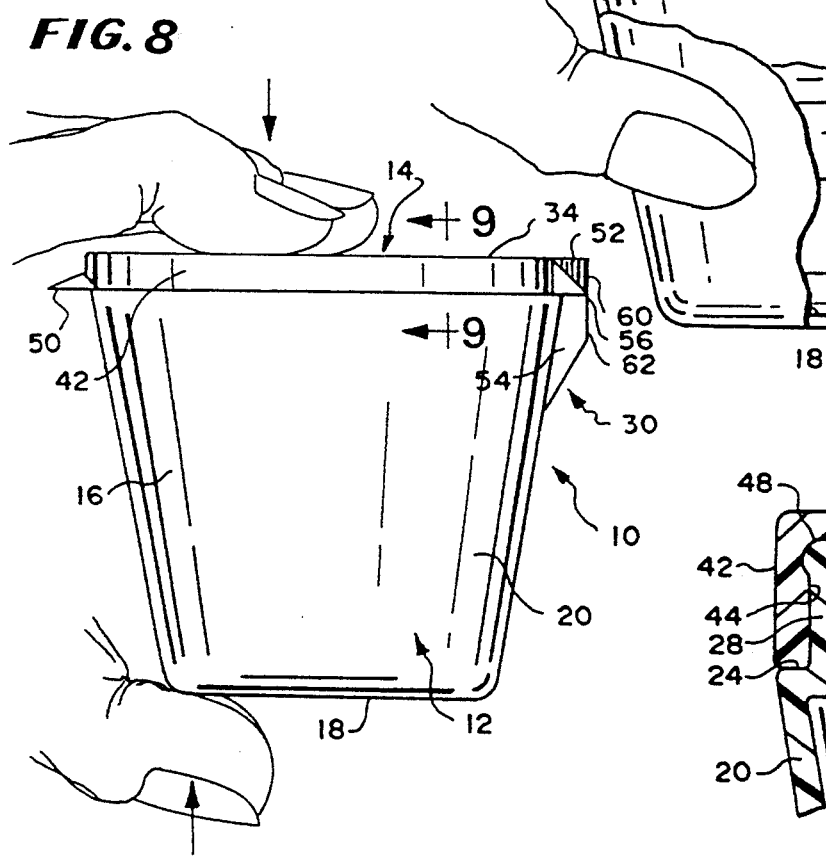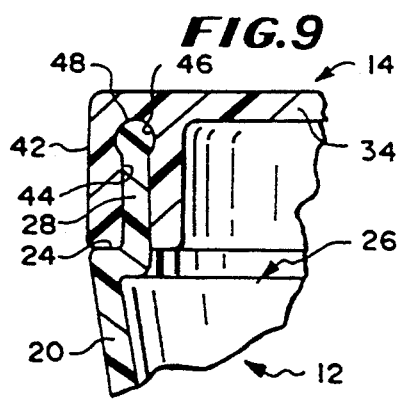

ASSEMBLIES FOR COLLECTING URINE AND OTHER BODY FLUIDS

This is a continuation of copending application Ser. No. 07/694,364 filed on May 1, 1991 now abondoned.

FIELD OF THE INVENTION

Our invention relates to fluid collection systems and devices. In a more specific sense, our invention also relates to systems and devices for collecting body fluids like urine.

BACKGROUND OF THE INVENTION

Health professionals have for many years examined body fluids to assess a person's physical health and fitness. Urine is one body fluid that has been routinely collected for analysis by health professionals. Today, employers are also beginning to collect urine specimens from present and prospective employees to detect potential substance abuse and other health related problems that can affect job performance.

In collecting urine and other body fluids, it is important to obtain uncontaminated samples. Aseptic collection techniques are therefore required. It is also important that the collection devices are easy to use by men, women, and children. Balanced against these largely medical and physiological requirements is the importance of providing collection devices at a reasonable, low cost.

There are many devices and system specially designed for the collection of urine and other body fluids. The following patents represent prior attempts in these and related areas:

Fazakerly U.S. Pat. No. 2,628,054
Giesy U.S. Pat. No. 3,335,714
Friedman et al U.S. Pat. No. 3,473,172
Munheim U.S. Pat. No. 3,575,225
Duyne U.S. Pat. No. 3,625,654
Collins U.S. Pat. No. 3,727,244
Geddes U.S. Pat. No. 3,927,426
Peterson Des. 258,311

Our invention aims to provide an improved system for collecting a body fluid like urine that meets the demands of aseptic collection techniques, ease of use regardless of sex or age, and low cost.

SUMMARY OF THE INVENTION

To achieve this and other objectives, our invention provides new systems for collecting urine and other body fluids. The systems that embody our invention promote aseptic techniques without sacrificing ease of use by members of both sexes and all ages. The systems are low cost and disposable.

Our invention provides an assembly for handling a urine collection container (or other containers for body fluids) in a straightforward and aseptic manner. The assembly includes a container having a chamber with an opening for receiving fluid and a lid for the container. When the lid is located in a first position, it overlies and closes the opening. The assembly also includes a hinge mechanism for attaching the lid to the container. Using the hinge mechanism, the user can move the lid in a first direction toward the first position to close the container and in a second direction away from the first position to open the container.

According to the invention, the hinge mechanism includes a bracing mechanism that abuts against and buttresses the lid against movement in the second direction beyond a preselected second position. When in its second position, the lid forms a outwardly extending handle that supports the container in a fixed upright attitude suited for receiving fluids.

According to the invention, the same structure attached to the container serves as both a lid and as a handle. The structure can be used as a handle to support and position the collection container as the sample is collected. The same structure can then be used as a lid to cover the collection container. The ready availability of the handle and cover promotes ease of use and aseptic techniques.

In a preferred arrangement, the container opening is generally elliptical or elongated in shape. This special shape simplifies use of the container by women. The presence of a handle for holding the container away from the user also simplifies its use by women.

In a preferred arrangement, the container includes a lip that surrounds the opening. In this arrangement the lid makes snap-fit engagement with the container lip when the lid overlies the container opening, further enhancing the improved aseptic benefits of the invention.

Other features and advantages of our invention will become apparent after considering the accompanying drawings, description, and claims.

DESCRIPTION OF THE DRAWINGS

FIG. 1 is a perspective view of a system for collecting body fluids such as urine that embodies the features of our invention, with the associated lid shown in its open and container supporting position;

FIG. 2 is a perspective view of the system shown in FIG. 1, with the associated lid in its closed position;

FIG. 3 is a side elevation view of the system shown in FIG. 1;

FIG. 4 is a side sectional view of the collection container associated with the system shown in FIG.3, taken generally along line 4—4 in FIG. 3;

FIG. 5 is a side sectional view of the lid associated with the system shown in FIG.3, taken generally along line 5—5 in FIG. 3;

FIG. 6 is a side section view of the system shown in FIG. 1 in the hand of the user, with the collection container supported by the attached lid in an upright and outwardly extended position away from the user's hand;

FIG. 7 is a side elevation view, with portions broken away and in section, of the system shown in FIG. 1, as the user moves the lid toward its closed position;

FIG. 8 is side elevation view of the system shown in FIG. 1, as the user places the lid into its closed and sealed position; and FIG. 9 is section view, taken along line 9—9 in FIG. 8, of the Junction between the lid and container when the lid is in its closed and sealed position.

DESCRIPTION OF THE PREFERRED EMBODIMENTS

FIGS. 1 to 3 show an assembly 10 for collecting body fluids that embodies the features of our invention.

The assembly 10 is applicable for use in the collection of different types of body fluids. The system 10 shown in the illustrated embodiment collects urine samples. However, we do not intend to limit the use of our invention just to collecting urine.

As shown in the drawings, the assembly 10 includes a collection container 12 for a body fluid. The collection container 12 can itself be conventional in construction and shape. It can be made of either glass or plastic materials. Preferably, the container 12 is a single use, disposable component of relatively low cost. So, the container 12 is preferably made of an inert plastic material, such as polyethylene. Conventional injection or blow molding techniques can be used to make the container 12. As an alternative, the container 12 can be made of a fluid resistant paper or paper composite material that is inert and biodegradable.

The container 12 includes a cup-shaped body 16 having a bottom wall 18 and an upstanding sidewall 20. The bottom wall 18 and sidewall 20 enclose an interior fluid chamber 22. The sidewall 20 terminates along an upper edge 24 forming an opening 26, through which fluids enter the chamber. In the illustrated and preferred embodiment, an upwardly extending lip 28 protrudes from the upper sidewall edge 24 (as FIG. 4 also shows). The function of this lip 28 will be described in greater detail later.

As best shown in FIG. 3, the sidewall 20 tapers outward from the bottom wall 18. As best shown in FIG. 1, the sidewall 20 is also elongated along one radial direction to form a generally elliptical shape. The elongated shape of the container 12 allows women to more easily use it.

In the illustrated embodiment, the container 12 holds about four (4) fluid ounces. Still, the volume of the container 12 can vary, according to the intended use, up to eight (8) ounces or more.

The assembly 10 includes a lid 14 for the container. The assembly also includes a hinge mechanism 30 that attaches the lid 14 to the container 12 for manipulation by the user.

More particularly, when urged by the user in a first direction, the lid 14 pivots about the hinge mechanism 30 toward a first position overlying the opening (as FIG. 2 shows). When urged by the user in a second direction, the lid 14 pivots about the hinge mechanism 30 out of the first position (as FIGS. 1 and 3 show). The user is thereby able to manipulate the lid 14 to open the container 12 for receiving fluids and to then close the container 12 after use.

The hinge mechanism 30 also includes means 32 for bracing the lid 14 in a preselected, outwardly extending position (as FIGS. 1; 3; and 6 best show). In this braced position, the lid 14 also serves as a weight bearing handle for supporting the container in use. FIG. 6 shows the lid 14 braced in a preferred container support position serving as a handle in the hands of a user.

Various constructions for the combination lid/handle 14 and associated hinge mechanism 30 are possible. In the illustrated embodiment, the lid 14 includes a main body 34 having oppositely spaced end portions 36 and 38. When the lid 14 is located in its first position (see FIGS. 2 and 8), the main body 34 overlies the top edge 24 of the container 12 to close the opening 26.

The lid 14 includes a skirt 40 that depends from the peripheral edge of the main body 34. In the illustrated embodiment (see FIG. 1), the skirt 40 wraps around the lid end portion 36 and converges toward the end portion 38. As FIG. 9 shows, when the lid main body 34 overlies the opening 26, the outer edge 42 of the skirt 40 is aligned in a generally coplanar relationship with the container edge 24 around the opening 26.

In the illustrated embodiment (see FIGS. 1 and 5), the skirt 40 includes an interior channel 44 formed in its undersurface. The channel 44 is arranged to register with the upstanding lip 28 of the container when the lid 14 is placed in its closed position (see FIG. 9). A keyway 46 formed in the base of the channel 44 makes snap fit engagement with a key 48 formed on the lip 28 to releasably secure the lid 14 in the closed position (as FIG. 9 shows). The snap-fit engagement seals the lid 14, when in its closed position.

In the illustrated embodiment, the outer edge 42 of the skirt 40 includes a gripping surface 50 formed at lid end portion 36 to allow the user to selectively break the snap fit engagement by pressing upwardly upon the lid 14.

The hinge mechanism 30 includes a first hinge tab 52 that protrudes outwardly from the skirt 40 at the lip end portion 38. The hinge mechanism 30 also includes a second hinge tab 54 that protrudes outwardly from the container edge 24. As FIGS. 2 and 8 best show, when the main body 34 of the lid 14 overlies the container opening 26, the first hinge tab 52 overlaps the second hinge tab 54. A flexible hinge joint 56 joins the overlapping hinge tabs 52 and 54.

In the illustrated embodiment, the hinge mechanism 30 also includes two hinge stiffening ribs 58. One end of each stiffening rib 58 joins the hinge joint 56 along opposite sides of the lid hinge tab 52. The other end of each stiffening rib 58 joins in the lid skirt 40. The hinge stiffening ribs 58 give added strength to the overall hinge mechanism 30.

In the illustrated embodiment, the bracing means 32 of the hinge mechanism 30 includes first and second bracing surfaces 60 and 62. The bracing surfaces 60 and 62 extend from opposite sides of the hinge joint 56. The first bracing surface 60 is associated with the lid hinge tab 52, and the second bracing surface 62 is associated with the container hinge tab 54.

When the lid 14 is in its closed position (as FIGS. 2 and 8 best show), the first and second bracing surfaces 60 and 62 extend in a generally coplanar relationship with the hinge joint 56. When the lid 14 is opened and moved into the preselected container supporting position, the first bracing surface 60 is successively folded over the hinge joint 56 and eventually brought into abutting contact against the second bracing surface 62 (as FIGS. 1, 3, and 6 best show). This abutting contact occurs when the lid 14 reaches its preferred outwardly extending position.

The abutting contact between the bracing surfaces 60 and 62 directs the weight load of fluid carried within the container 12 away from the flexible hinge Joint 56 onto the lid 14 itself. In effect, the bracing surfaces 60 and 62 buttress the lid 14 when it assumes the preferred outwardly extending position. This buttressing transforms the open lid 14 into a cantilevered, weight bearing handle that can be readily grasped and used to hold the container 12 in a fluid receiving upright position away from the user's hand during use.

The lid 14 and hinge mechanism 30 are preferably made of generally rigid materials. The term "generally rigid" means that the lid 14 and hinge mechanism 30 will not easily bend or break under the weight of the container 12 when fully filled with fluid and handled in the manner described in this application. The term "generally rigid" encompasses both inflexible and rigid materials. The term also encompasses materials that are semi-flexible or resilient, if they have the strength to support and handle the weight of the container 12 in the manner described in this application.

The lid 14 and hinge mechanism 30 can be made of the same inert plastic material as the container 12, such as polyethylene. In this arrangement, the lid 14 and hinge mechanism 30 can be integrally molded parts of the container 12 formed using conventional injection or blow molding techniques.

Alternatively, the lid 14 and hinge mechanism 30 can be manufactured separately from the container 12 and later affixed to the container 12 by solvent or adhesive bonding techniques or the like. In this arrangement, the lid and hinge mechanism can be made of the same or a different material as the container 12, provided the materials are sufficiently compatible to allow attachment of the lid and hinge mechanism to the container 12.

In use, the user moves the lid 14 to the outwardly extended position before collecting fluid. As FIG. 6 shows, the user holds the lid 14 as a handle to position the container 12 while introducing fluid into the container. The abutting bracing surfaces 60 and 62 assure that the container 12 will be retained in a stable upright position away from the user's hands (as FIG. 6 shows).

Once fluid is collected in the container 12, the user can grasp the container 12 in one hand and the lid 14 in another (as FIG. 7 shows). The user then moves the lid 14 into the closed position, applying pressure as needed to bring the lip into snap-fit engagement with the lid 14 channel (as FIGS. 7 and 8 show).

The container 12 is now closed and sealed for transport and storage. The lid 14 can be later opened for access to the fluid up pressing upwardly upon the gripping surface 50.

The assembly 10 that embodies the features of the invention assure that the entire fluid collection procedure is performed in a convenient, aseptic manner.

The following claims set forth the features and advantages of our invention.

We claim:

1. An assembly for collecting urine and other body fluids comprising:
   a container haivng a chamber with an opening for receiving fluid and having a first buttress extending laterally from a surface thereof,
   a lid for the container that, when located in a first position, overlies the opening, said lid having a second buttress aligned with said first buttress, and
   means for supporting the weight of the container and body fluids contained therein, said means comprising a hinge attaching the lid to the container for movement by the user in a first direction toward the first position to close the container and in a second direction away from the first position to open the container, the hinge connecting the outermost edges of said first and second buttress and causing them to pivot into abutting contact with each other to brace the lid against movement in the second direction beyond a preselected second position in which the lid forms a outwardly extending handle that supports the weight of the container and its contents in a fixed upright attitude during use.

2. An assembly according to claim 1
   wherein the container includes a lip that surrounds the opening, and
   wherein the lid includes means for sealingly engaging the container lip when the lid overlies the container opening.

3. An assembly according to claim 1
   wherein the container includes a lip that surrounds the opening, and
   wherein the lid includes means for making snap-fit engagement with the container lip when the lid overlies the container opening.

4. An assembly according to claim 1
   wherein the opening of the container is generally elliptical in shape.

5. An assembly according to claim 1
   wherein the opening of the container is generally elongated in one radial direction,
   wherein, when the container supported by the handle, the elongated radial direction of the container extends toward the handle.

6. An assembly for collecting urine and other body fluids comprising
   a container having a sidewall that forms a fluid receiving chamber having an opening,
   a lid formed of one piece with said container and having a main body portion that, when the lid is located in a first position, overlies the opening, the lid further including a skirt that depends from the main body portion,
   means for supporting the weight of the container and body fluids contained therein, said means comprising a hinge mechanism integral with and attaching the lid to the container for movement in a first direction toward the first position and in a second directin toward a second position in which the lid extends outwardly from the container, the hinge mechanism including a first bracing surface associated with the lid and a second bracing surface associated with the container, said first and second bracing surfaces being coplanar with a connecting hinge joint which joins said surfaces at their outer perimeters and the first and second bracing surfaces being located on opposite sides of the hinge joint in generally the same plane when the lid is in its first position, the first and second bracing surfaces being brought into facing abutting contact when the lid is moved in its second direction into the preselected second position to transform the lid into a handle that supports the weight of the container and its fluid contents in an upright position away from the user's hand during use.

7. An assembly according to claim 6
   wherein the container includes a lip that surrounds the opening, and
   wherein the lid includes means for sealingly engaging the container lip when the main body of the lid overlies the container opening.

8. An assembly according to claim 6
   wherein the container includes a lip that surrounds the opening, and
   wherein the lid includes means for making snap-fit engagement with the container lip when the main body of the lid overlies the container opening.

9. An assembly according to claim 6
   wherein the opening of the container is generally elliptical in shape.

10. An assembly according to claim 6
    wherein the opening of the container is generally elongated in one radial direction,
    wherein, when the container supported by the handle, the elongated radial direction of the container extends toward the handle.

* * * * *